United States Patent [19]
Yagi et al.

[11] Patent Number: 5,348,630
[45] Date of Patent: * Sep. 20, 1994

[54] METHOD OF MEASURING HUMIDITY USING AN ELECTROCHEMICAL CELL

[75] Inventors: Hideaki Yagi; Katsuhiko Horii, both of Nagoya, Japan

[73] Assignee: NGK Spark Plug Co., Ltd., Nagoya, Japan

[ * ] Notice: The portion of the term of this patent subsequent to Jun. 2, 2009 has been disclaimed.

[21] Appl. No.: 896,503

[22] Filed: Jun. 2, 1992

Related U.S. Application Data

[63] Continuation of Ser. No. 439,092, Nov. 20, 1989, abandoned.

[30] Foreign Application Priority Data

| | | |
|---|---|---|
| Nov. 29, 1988 [JP] | Japan | 63-155024[U] |
| Nov. 29, 1988 [JP] | Japan | 63-301908 |
| Nov. 29, 1988 [JP] | Japan | 63-301909 |

[51] Int. Cl.$^5$ .................................. G01N 27/406
[52] U.S. Cl. .................. 204/153.22; 204/426; 204/429
[58] Field of Search .......... 204/153.18, 153.22, 204/421–429, 430

[56] References Cited

U.S. PATENT DOCUMENTS

| | | | |
|---|---|---|---|
| 3,691,023 | 9/1972 | Ruka et al. | 204/153.18 |
| 4,158,166 | 6/1979 | Isenberg | 204/153.18 |
| 4,272,350 | 6/1981 | Croset et al. | 204/426 |
| 4,310,401 | 1/1982 | Stahl | 204/426 |
| 4,356,065 | 10/1982 | Dietz | 204/153.18 |
| 4,416,763 | 11/1983 | Fujishiro | 204/429 |
| 4,502,939 | 3/1985 | Holfelder et al. | 204/429 |
| 4,505,807 | 3/1985 | Yamada | 204/426 |
| 4,574,627 | 3/1986 | Sakurai et al. | 204/426 |
| 4,578,174 | 3/1986 | Kato et al. | 204/427 |
| 4,851,103 | 7/1989 | Usami et al. | 204/425 |
| 5,080,765 | 1/1992 | Wang et al. | 204/425 |

*Primary Examiner*—T. Tung
*Attorney, Agent, or Firm*—Cooper & Dunham

[57] ABSTRACT

In a method of measuring humidity by using an electrochemical cell, the method comprises applying a voltage across the pair of electrodes to obtain a characteristic curve between the voltage applied and electrical current. The characteristic curve starts with a first flat portion in which a first diffusion limit current remains generally constant within a predetermined voltage range and passes through a point of inflection in which a second differential derivative of the characteristic curve falls on zero at certain voltage, and ends up with a second flat portion in which a second diffusion limit current remains generally constant within a predetermined voltage range. The point of the inflection is uniquely determined regardless of a humidity level of the gas at a constant temperature and oxygen concentration. The humidity level in the gas is obtained by reading the point of the inflection, and the intensity of the first and second diffusion limit current and then comparing the diffusion limit current with the inflection as a reference current.

8 Claims, 10 Drawing Sheets

METHOD OF MEASURING HUMIDITY USING AN ELECTROCHEMICAL CELL

This is a continuation of application Ser. No. 439,092, filed Nov. 20, 1989, now abandoned.

BACKGROUND OF THE INVENTION

1. Field of the Invention

This invention relates to a humidity measurement device in which humidity in an atmosphere is measured by using an electrochemical cell.

2. Description of the Prior Art

In a humidity measurement device of this type, there have been devices known in Japanese Provisional Publication Patent Nos. 60-222761, 62-150151 and 62-150152.

In the Japanese Provisional Publication Patent No. 60-222761, partial pressure of oxygen component in a gas is measured with the function of limit currents, each value of which is obtained before and after removing aqueous vapor component from the gas.

The Japanese Provisional Publication Patent No. 62-150151 teaches that the limit currents due to gas diffusion are obtained depending on an oxygen density and an aqueous density in the gas. The difference between values of the limit currents leads to humidity measurement.

Further, the Japanese Provisional Publication Patent No. 62-150152 suggests that a first limit current due to the oxygen density and a second limit current due to the aqueous density are obtained. Then a third limit current based on a dehumidified gas is obtained. The humidity is measured based on the difference between the third limit current and at least one of the first and second limit currents.

In each device according to the Japanese Provisional Publication Patent Nos. 60-222761, 62-150151 and 62-150152, however, a dryer device is required to desiccate so as to remove aqueous vapor from the gas atmosphere, simultaneously a measurement device is required to measure the limit current. Thus necessitates a large scale measurement system as a whole resulting in a slow operation of the humidity measurement.

Therefore, the invention has its object to provide a humidity measurement device which is capable of eliminating all the drawbacks mentioned above.

It is an object of the invention to provide a humidity measurement device which is capable of measuring humidity level with a high accuracy.

It is an object of the invention to provide a compact humidity measurement device which is capable of measuring humidity with a quick response.

SUMMARY OF THE INVENTION

According to the invention there is provided a humidity measurement device comprising;

an electrochemical cell made of solid electrolyte having an oxygen-ion conductive property;

a pair of porous electrodes provided in tight contact with the surface of the solid electrolyte;

a gas diffusion limiting aperture provided such that one of the electrode is partly exposed to a gas such as atmosphere to limit an oxygen component in the gas from being diffused through the aperture into said one of the electrodes;

a heater provided to heat the electrodes;

a voltage being impressed across the electrodes to result in a characteristic curve between the voltage and a current flow across the electrodes, the characteristic curve characterizing continuously a first flat portion in which a first diffusion limit current remains generally constant within a first predetermined voltage range, passing through a point of an inflection current in which second differential derivative of the characteristic curve falls on zero, and ending up in a second flat portion in which second diffusion limit current remains generally constant within a second predetermined voltage range; and a humidity in the gas being given by comparing the inflection current with either of the first and second currents.

The characteristic curve is such that the increase of the humidity decreases the first diffusion limit current (IL1) in the flat portion (F1) when the voltage impressed is below the point of an inflection voltage (VM), at the point of inflection the inflection current (IM) remains constant under an unchanged density of oxygen in the gas irrespective of how the humidity changes, and when the voltage is beyond the point of the inflection voltage (VM), the humidity increases the second diffusion limit current (IL2) in the flat portion (F2) as seen in FIG. 6.

In the manufacture of humidity measurement devices of the invention, a reference current level for each electrochemical cell is predetermined by the inflection current which is given by the point where the characteristic curves which appear under at least two different humidity conditions of an oxygen-constant atmosphere make an intersection, since the inflection current does not vary regardless of the temperature as long as the gas to be measured maintains the same level of oxygen density. This inflection current of the electrochemical cell indicates always the reference current level corresponding to a zero humidity level of the gas having a constant level of the oxygen density.

Although the inflection point is expressed also by the inflection voltage (VM), according to the invention upon humidity measurement the inflection current to be previously memorized as the reference current level is compared with either of the diffusion limit currents (IL1), (IL2) which are obtained just by impressing either of the first and second predetermined voltages, corresponding to the flat portions (F1) and (F2) respectively separated by the inflection voltage (VM).

Even in the case that the density of oxygen in the aqueous atmosphere changes, the humidity can be quickly and easily determined, according to the invention, by alternately changing the voltage applied across the electrodes from the voltage at the point of inflection (P) to assure or rather adjust the inflection current for the zero-humidity reference level to the voltage of either of the flat portions (F1) and (F2) to measure the diffusion limit current (IL1) or (IL2) for the comparison and comparing the adjusted inflection current with the measured diffusion limit current to compute the humidity of the gas in a comparatively short time.

These and other objects and advantages of the invention will be apparent upon reference to the following specification, attendant claims, and drawings.

DETAILED DESCRIPTION OF THE INVENTION

Figure 1:
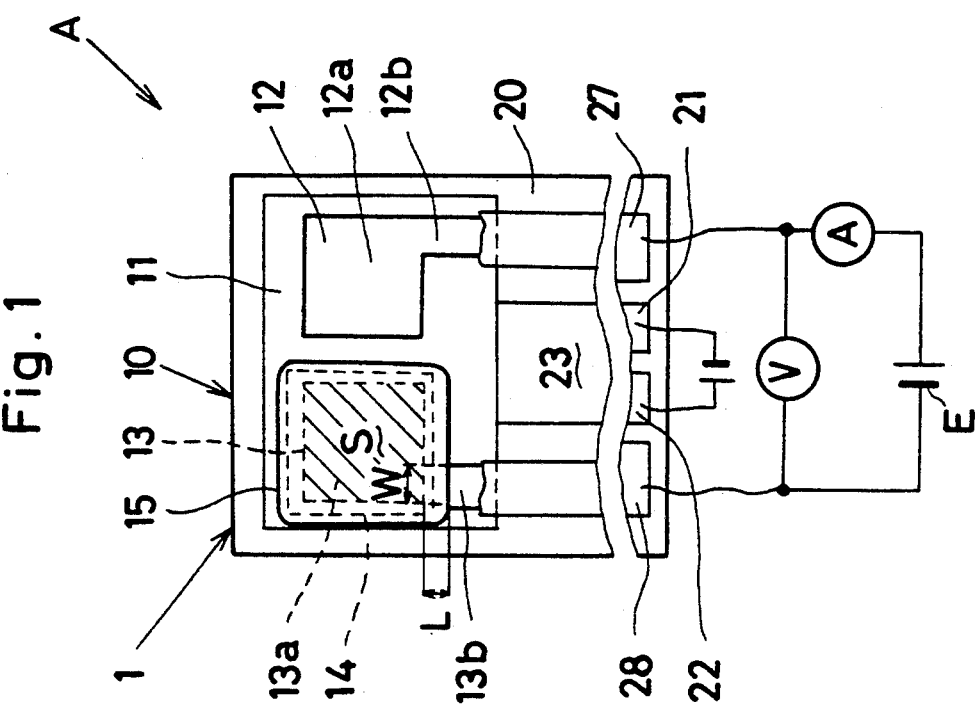
FIG. 1 is a schematic view of humidity measurement device embodied by the present invention.

Referring to FIG. 1 through FIG. 4 in which a solid electrolyte electrochemical cell 1 according to one of the embodiment of the invention is shown. The electrochemical cell 1 has a sensor element 10 and a ceramic heater 20. The sensor element 10 comprising an oxygen-ion conductive plate 11, and an anode electrode 12, a cathode electrode 13, an alumina porous layer 14 and a glaze layer 15.

Figure 3:
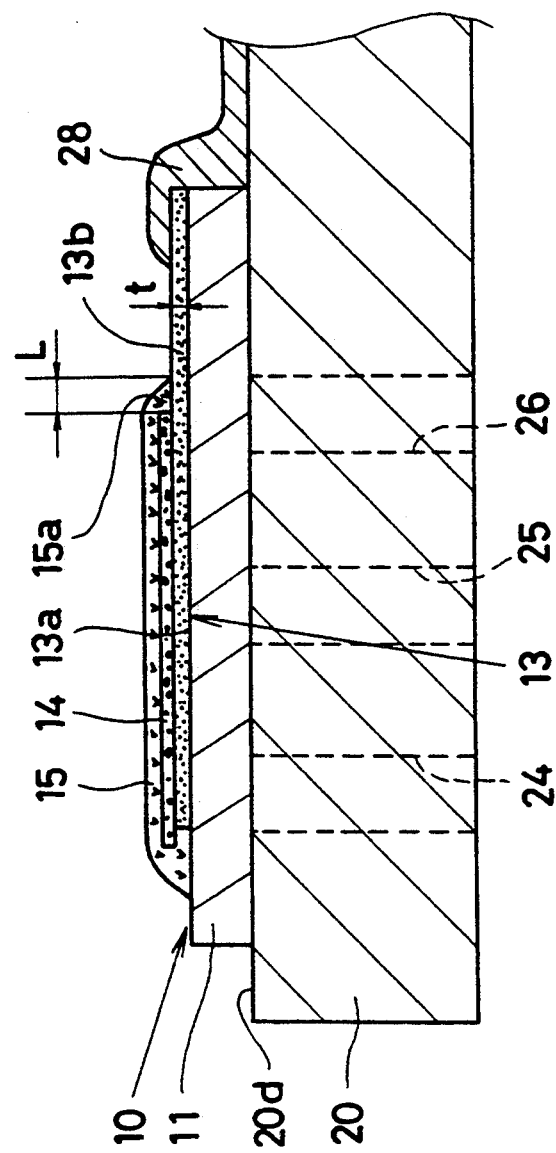
FIG. 3 is a cross-sectional view of the electrochemical cell.

The oxygen-ion conductive plate 11 is made of a solid solution of zirconia partially stabilized with yttrium oxides to serve as a solid electrolyte. The oxygen-ion conductive plate 11 according to one of the embodiment of this invention, is in the shape of rectangle, and measured as 5 mm×7 mm, and having a thickness of 0.3 mm. On a top surface of the oxygen-ion conductive plate 11, the anode and cathode electrode 12, 13 are located at the predetermined parallel interval, each of which has electrode portions 12a, 13a and connection portions 12b, 13b. Each of the electrodes 12, 13 is made of porous platinum sintered on the oxygen-ion conductive plate 11 at the temperature of 1500 degrees centigrade after they are printed on the plate 11. On the oxygen-ion conductive plate 11, the alumina porous layer 14 which contains some glass (not shown) is coated in a manner to cover the electrode portions 13a and partly cover the connection portions 13b. The glaze layer 15 covers the alumina porous layer 14 in order to prevent the electrode portion 13a from being exposed to the gas to be measured except at the connection portion 13b. The alumina porous layer 14 and the glaze layer 15 thus coated on the oxygen-ion conductive plate 11 are made by firing the layers 14, 15 at the temperature of 850– 900 degrees centigrade The electrode portion 13a is isolated from the gas, but the connection portion 13b is not covered by the glaze layer 15 as seen in FIG. 3.

Since the connection portion 13b is exposed at one end of the glaze layer 15 to the gas, the connection portion 13b is equivalent to a gas diffusion limiting aperture which limits both oxygen diffusion and aqueous vapor diffusion towards the electrode portion 13a when voltage is impressed across the electrodes 12, 13. Each of the electrodes 12, 13 has a thickness (t) of 20 microns, and the electrode portions 12a, 13a are in the shape of square of 2.5 mm×2.5 min.

The connection portion 13b has a width (W) of 1 mm, and a length (L) of 2 mm covered partly by the glaze layer 15.

The amount of gas diffusion towards the electrode portion 13a through the connection portion 13b is in proportion to the cross sectional area ( s; not shown ) but in inverse proportion to the length (L) of the connection portion 13b, where the cross sectional area (s) is given by the product of the width (W) and thickness (t; not shown) of the connection portion 13b which acts as a gas diffusion limiting aperture in this embodiment.

A practical ratio (R) by which the diffusion limit currents can be controlled is determined with the cross sectional area (s) of the connection portion 13b, the surface area (S) of the electrode portion 13a and the length (L) as follows:

$$R = s/L/S = 1 \times 10^{-5} - 8 \times 10^{-2}$$

According to the embodiment of this invention, the formula $R = 1.6 \times 10^{-3}$ is obtained since the relationship among (s), (L) and (S) are $s = 0.02$, $L = 2$, $S = 6.25$ in turn.

Figure 4:
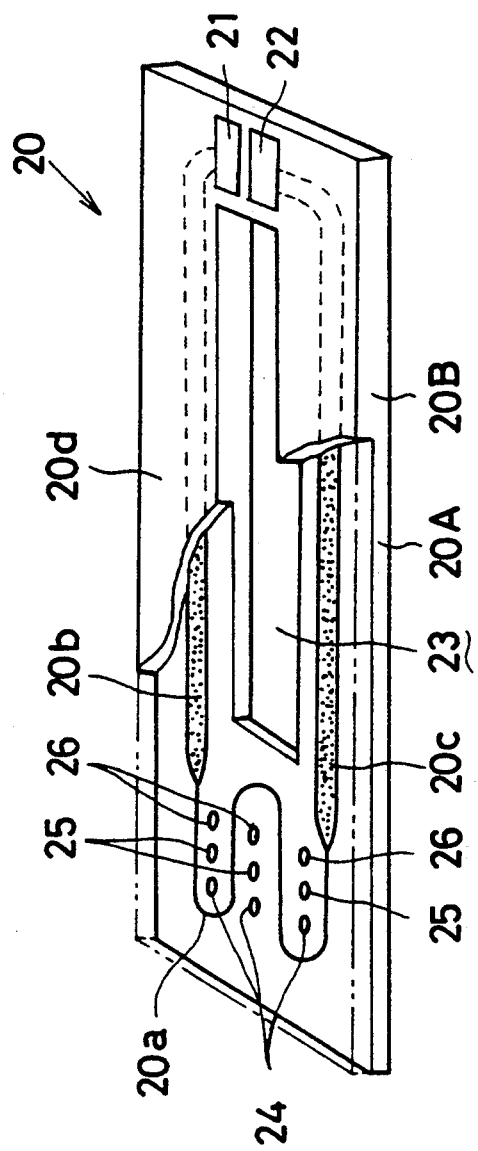
FIG. 4 is a perspective view of a ceramic heater illustrated partly in FIG. 2.

In the meanwhile, the sensor element 10 is bonded on the ceramic heater 20, with vitreous adhesives (not shown) and baked together at the temperature of circa 800 degrees centigrade. The ceramic heater 20 is a substrate heater, as shown in FIG. 4, manufactured by firing a green sheet 20A made of 96% alumina on which an appropriate heater pattern 20a is previously made by printing tungsten (wolfram) paste and a green sheet cover 20B identical to the green sheet 20A being laminated together.

The heater pattern 20a is connected at their respective ends to heater-electrodes 21, 22 on an outside surface 20d by way of conductive patterns 20b, 20c sintered inside the ceramic heater 20.

Since action of the gas diffusion limiting is effected at the connection portion 13b of the cathode electrode 13 in accordance with the invention, the heater pattern 20a is adapted to locally heat the electrode portions 12a, 13a which pump oxygen in and out, thus preventing an oxygen pumping due to the connection portion 13b which keeps comparatively a low temperature.

In the meanwhile, the ceramic heater 20 has a central opening 23 to enhance the heating efficiency against the sensor element 10, and a plurality of rows of perforations 24, 25 and 26 are made in the area where the sensor element 10 is placed. On the surface 20d of the ceramic heater 20, there is provided sensor electrodes 27, 28 which are in turn connected to the connection portions 12b, 13b by means of ruthenium printed pattern for energization of the electrodes 12, 13. The sensor electrodes 27, 28 are printed and sintered simultaneously on the ceramic heater 20 and the sensor element 10 after the sensor element 10 is bonded on the surface 20d.

The electro-chemical cell 1, thus constructed, is adapted to serve as a sensing portion of the humidity measurement device (A) to measure voltage and current when voltage is impressed across the sensor electrodes 27, 28 by means of a power source (E). In this instance, the ceramic heater 20 is energized to heat around the electrode portions 12a, 13a to keep them at the temperature of 300–700 degrees centigrade.

Figure 6:
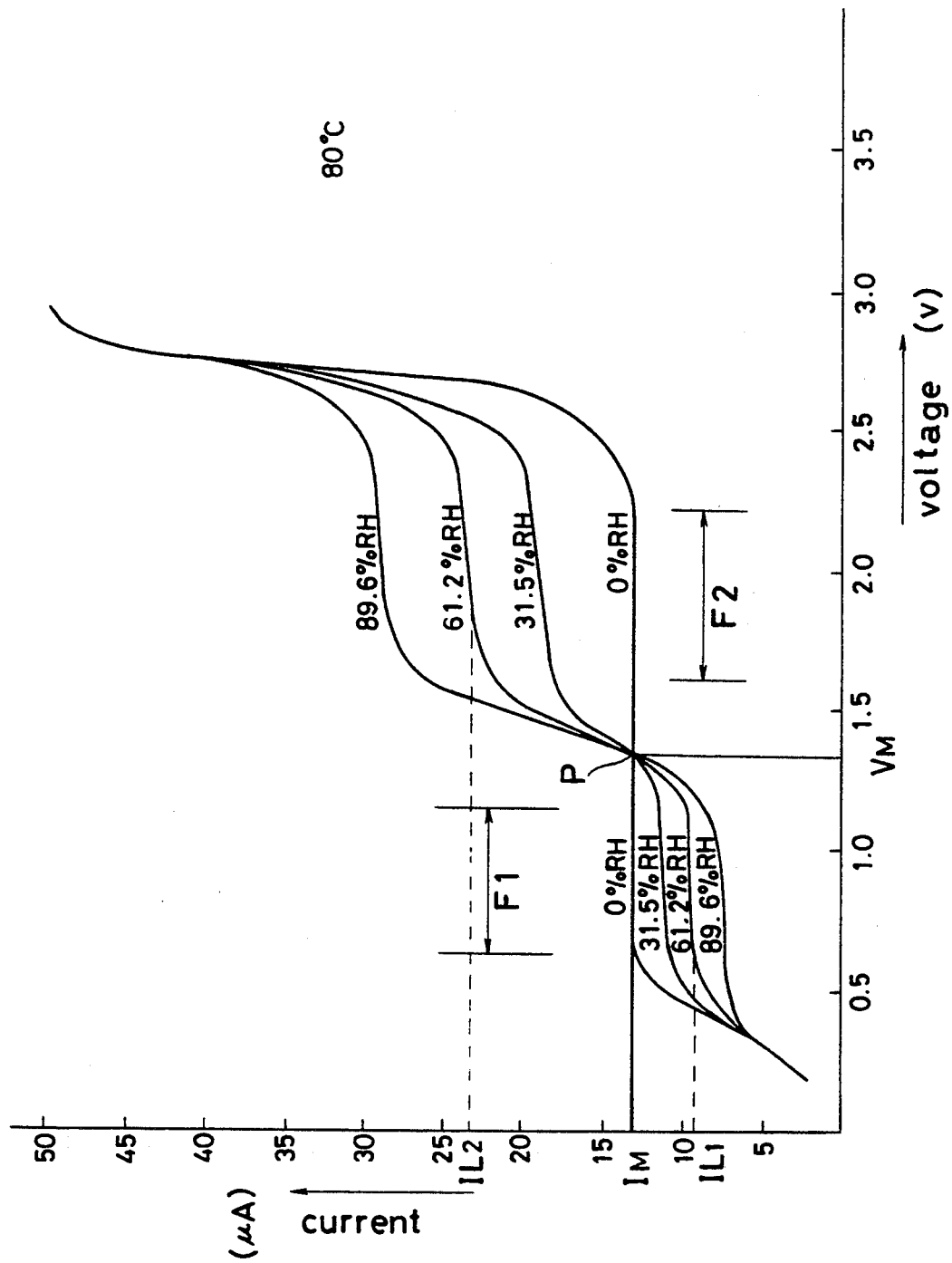
FIG. 6 is a view of characteristic curves showing the relationship between voltage and current in the humidity measurement device of the present invention.

With the structure thus described, the electro-chemical cell 1 is placed in the gas to be measured. The voltage impressed across the electrodes 12, 13 causes to ionize oxygens in the electrode portion 13a covered by the glaze layer 15, and as a result the oxygen component in the gas which comes through the gas diffusion aperture of the porous connecting portion 13b is pumped from the cathode electrode 13 to the anode electrode through the sensor element 10 of oxygen-ion conductive solid electrolyte in accordance with the voltage impressed across the electrodes 12, 13. At this time, only the electrode portion 13a is locally heated so that the oxygen component diffuse into the electrode portion 13a through the connection portion 13b which is not heated. The diffusion amount of oxygen component into the electrode portion 13a is limited by the gas diffusion limit aperture of the connection portion 13b in accordance with the density of the oxygen in the gas to be measured The limited amount of gas diffusion accompanies with current restriction to be represented as the first diffusion limit current (IL1) or the second diffusion limit current (IL2) as seen in the range of the first flat portion (F1) or the second flat portion (F2) in FIG. 6 in which the temperature of the gas to be measured stands at 80 degrees centigrade. In FIG. 6, characteristic curve are depicted between the voltage and the current flow across the electrodes under various humidity levels. The curve continuously originates from the first flat portion (F1) in which the first diffusion current (IL1) remains substantially constant within the first predetermined voltage range, and passes through a point of inflection (P) at which its second differential derivative falls on zero, and ends up in the second flat portion (F2) in which the second diffusion limit current (IL2) remains substantially constant within the second predetermined voltage range.

The first diffusion limit current (IL1) which is lower than the inflection current (IM) decreases with the increase of aqueous or rather humidity density of the gas simply because a partial pressure of the oxygen component decreases with the increase of the aqueous density in the gas to be measured. When the impressed voltage increases at its magnitude higher than the inflection voltage (VM), the second diffusion limit current (IL1), increases with the increase of the aqueous density of the gas, because the aqueous component of $H_2O$ in the gas is dissolved to produce additional oxygen-ions which are pumped together to the anode electrode 12 from the cathode electrode 13. Although the aqueous component which diffuses into the electrode portion 13a through the connection portion 13b is controlled or rather limited to thereby make the current level (IL2) flat or constant in the predetermined voltage the aqueous density of the gas increases the level of the second diffusion limit current.

Since the oxygen diffusion and aqueous diffusion are limited at the connection portion 13b of the cathode electrode 13, the limit current (IL2) increases in proportion to the humidity while the limit current (IL1) increases in inverse proportion to the humidity under a constant density of oxygen component in the gas to be measured. However the point of inflection is not affected by the humidity of the gas so that the humidity measurement device according to the invention utilizes this point of inflection as the reference level of the humidity for the device.

When the impressed voltage is changed from that of the limit current (IL1) to that of the limit current (IL2), the inflection current level (IM) at the point of inflection at which the current switches from the limit current (IL1) to the limit current (IL2) does not change or move if the density of the oxygen gas is kept constant regardless of whether the aqueous density changes in the gas in which the electro-chemical cell is exposed.

The current level (IM) shows constant at the constant density of the oxygen, and it is noted that the value of the inflection current (IM) equally corresponds to the current when the aqueous density is zero (0% in relative humidity), that is; in the state of a complete desiccation.

The humidity measurement for the gas according to the invention is done as follows. By impressing the voltage around the inflection voltage (VM) corresponding to the point of inflection (P) across the sensor electrodes 27, 28, the inflection current (IM) is measured. Then, the voltage corresponding to either of the first flat portion (F1) and the second flat portion (F2) which are separated by the inflection voltage (VM) is impressed across the sensor electrodes 27, 28 to measure the diffusion limit current level (IL1 or IL2). Either of the current levels is compared with the inflection current to determine a relative humidity (aqueous density).

In this instance it is only necessary to measure the diffusion limit current level at either one of the first flat portion (F1) or the second flat (F2) for the comparison if the oxygen density in the gas to be measured is constant, once the inflection current (IM) at the inflection point (P) is determined for the zero humidity reference level, thus leading to good response of measurement with easy operation.

In the humidity measurement device according to the invention, it is only necessary to measure the inflection current level (IM) at the point of inflection (P) and thereafter to measure the current level at the flat portion, in the case in which there is a possibility that the density of oxygen in the gas to be measured is subjected to change.

Figure 7:
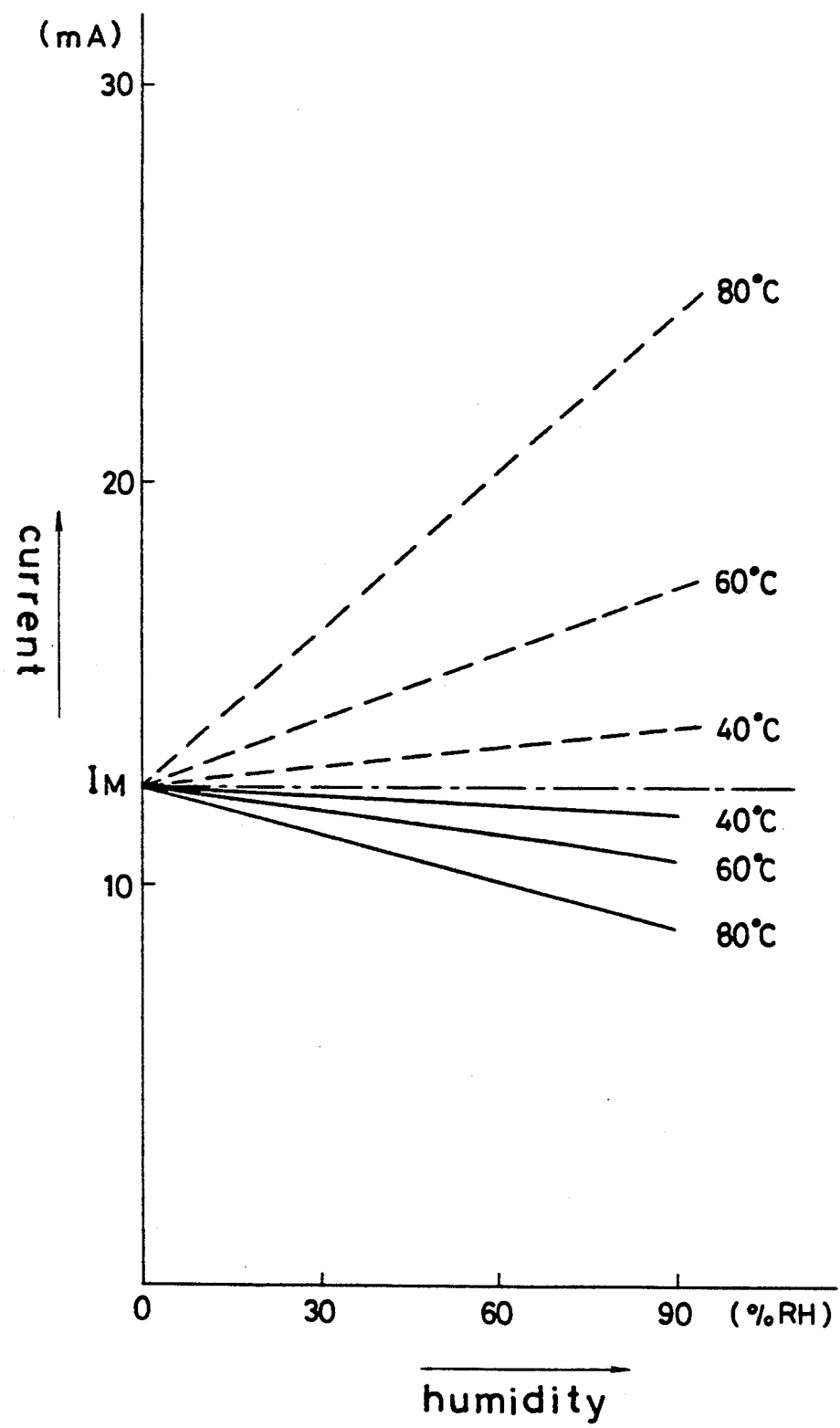
FIG. 7 is a view of characteristic curves showing the relationship between current and humidity in the humidity measurement device of the present invention.

FIG. 6 shows characteristic curves between the relative humidity and the current levels (IL1), (IL2) at the first and second flat portions (F1), (F2) under a constant density of oxygen component in the gas. In FIG. 7, the limit current levels (IL1) at the first flat portion (F1) are shown in solid line, while the limit current levels (IL2) at the second flat portion (F2) are shown in broken lines when the temperature of the gas component to be measured changes to 40, 60 and 80 degrees centigrade in turn. The dot-dash lines in FIG. 7 shows a current level (IM) at the point of inflection (P). It is understood by FIG. 7 that the inflection current (IM) can be used as the reference current of zero humidity under any temperature of the gas to be measured.

Figure 8:
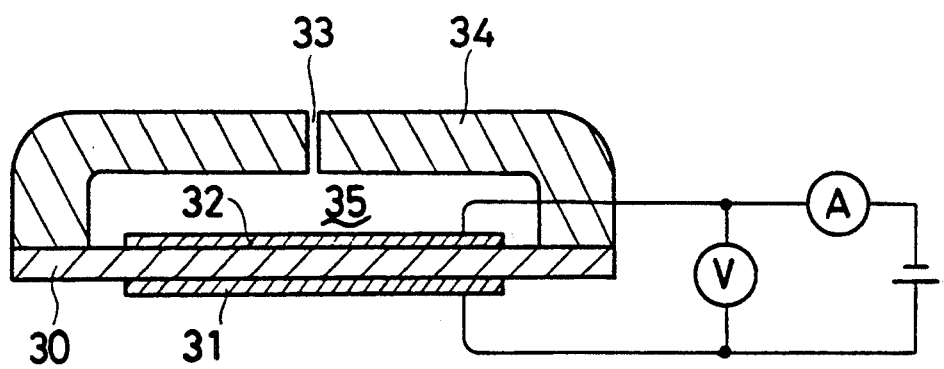
FIG. 8 is a schematic view of an oxygen measurement to which the present invention is applicable.
Figure 9:
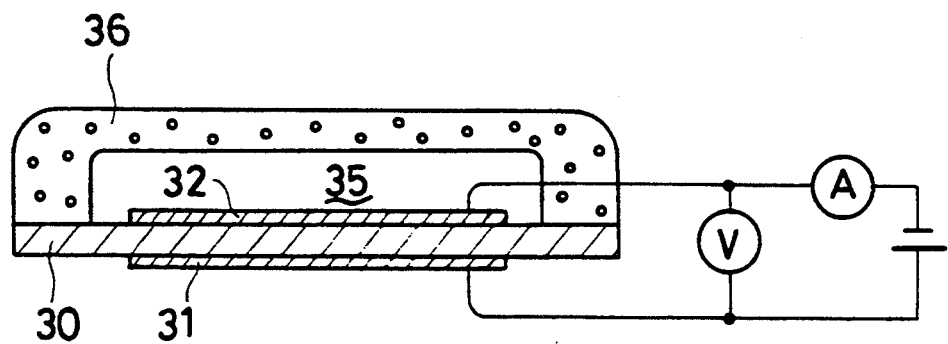
FIG. 9 is a schematic view of another oxygen measurement to which the present invention is applicable.

It is noted that electrodes 31, 32 may be placed in a manner to sandwich an oxygen-ion conductive plate 30 as seen in FIG. 8 wherein the cathode electrode 32 is covered by a coverlet 34 having a small perforation 33 which works to effect a vapor diffusion limiting action and a oxygen gas diffusion limiting action toward a hollow space 35. The cathode electrode 32 may be covered by a porous coverlet 36 to effect the vapor diffusion limiting action and the oxygen gas diffusion limiting action toward the hollow space 35 as seen in FIG. 9.

Figure 2:
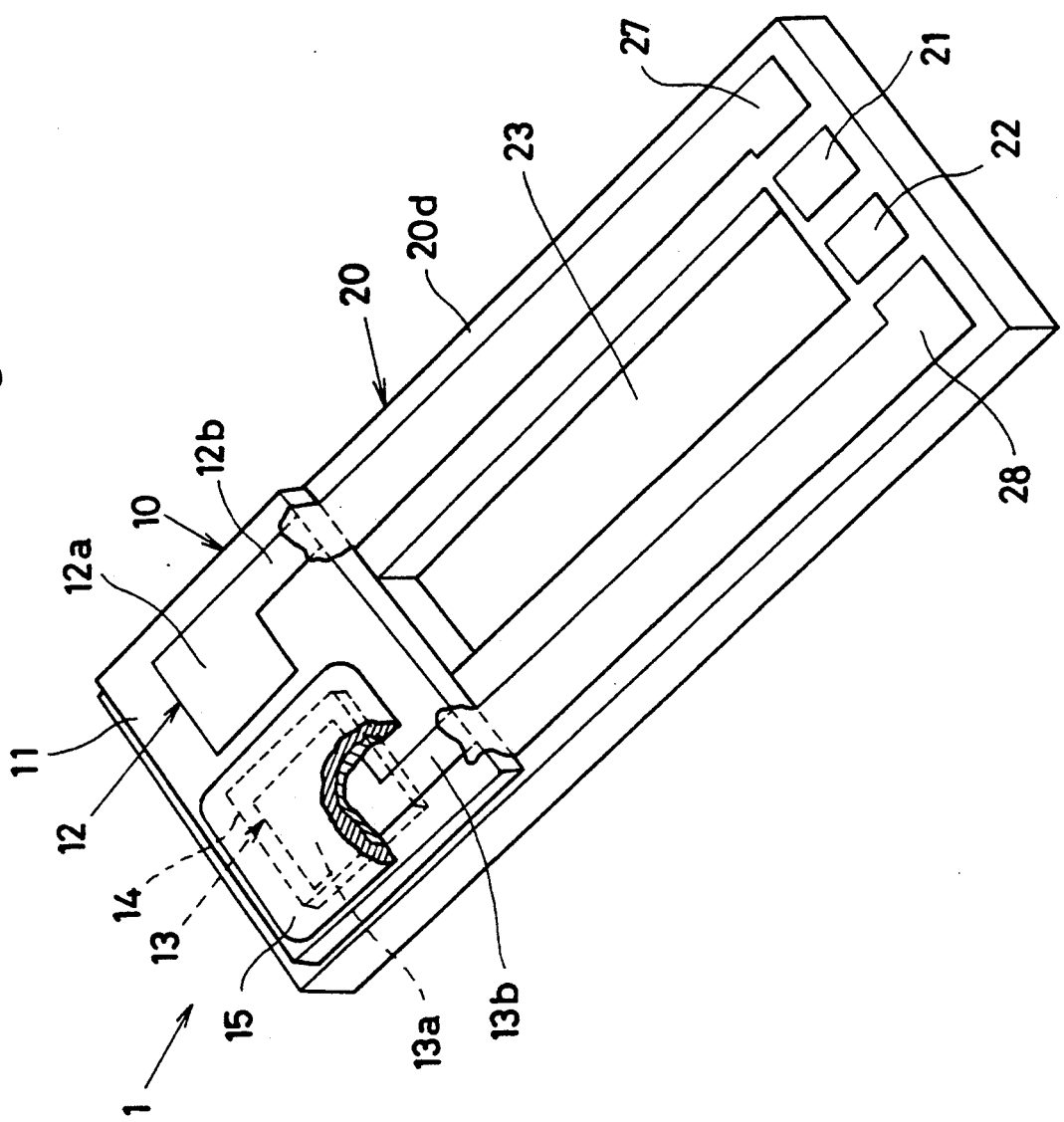
FIG. 2 is a perspective view of an electrochemical cell of the humidity measurement device shown in FIG. 1.
Figure 5:
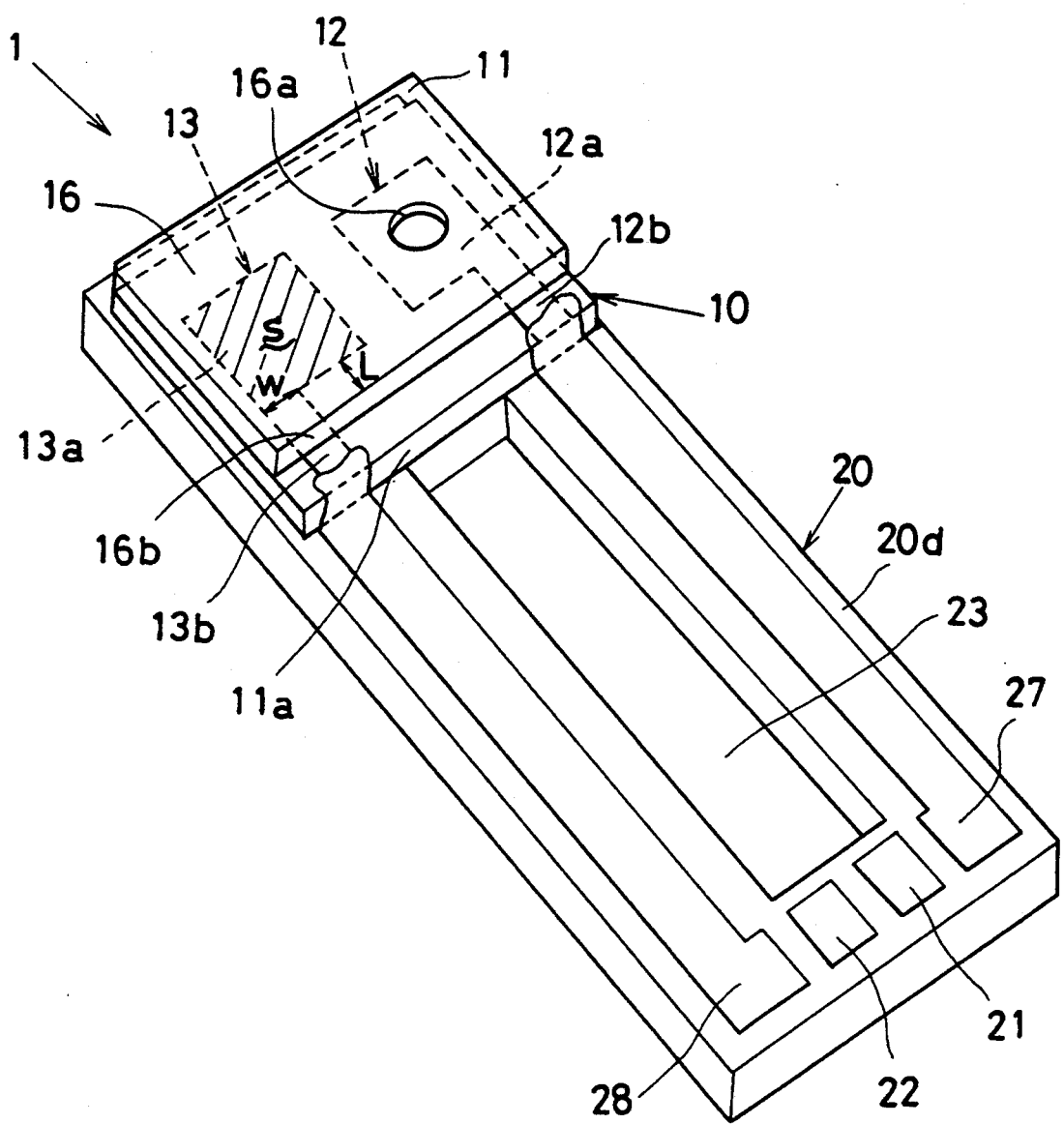
FIG. 5 is a perspective view of a modified type of the electrochemical cell shown in FIG. 2.

Referring now to FIG. 5 which shows a modification form of FIG. 2, instead of the alumina porous layer and the glaze layer 15 of FIG. 2, a cover plate 16 is provided in air-tight relationship with the oxygen-ion conductive plate 11. The cover plate 16 is in the form of rectangle having the same width as that of the oxygen-ion conductive plate 11, and terminating lengthwisely somewhat short of one end 11a of the oxygen-ion conductive plate 11.

In this instance, the connection portion 13b which sandwiched between the oxygen-ion conductive plate 11 and one end 16b of the cover plate 6, works as an oxygen gas diffusion limiting means. The plate 16 is preferably made of a solid electrolyte of zirconium partially stabilized with yttrium oxides, which has good wetting relationship with the oxygen-ion conductive plate 11 and the electrodes 12, 13 so as to facilitate ready bonding during the baking process.

The plate 16 further has a hole 16a which simply communicate the anode electrode portion 12a with the atmosphere to be measured.

It is noted that in the above modification form, the reference numerals corresponding to the elements in FIG. 2 are identical to those of FIG. 5.

Figure 10:
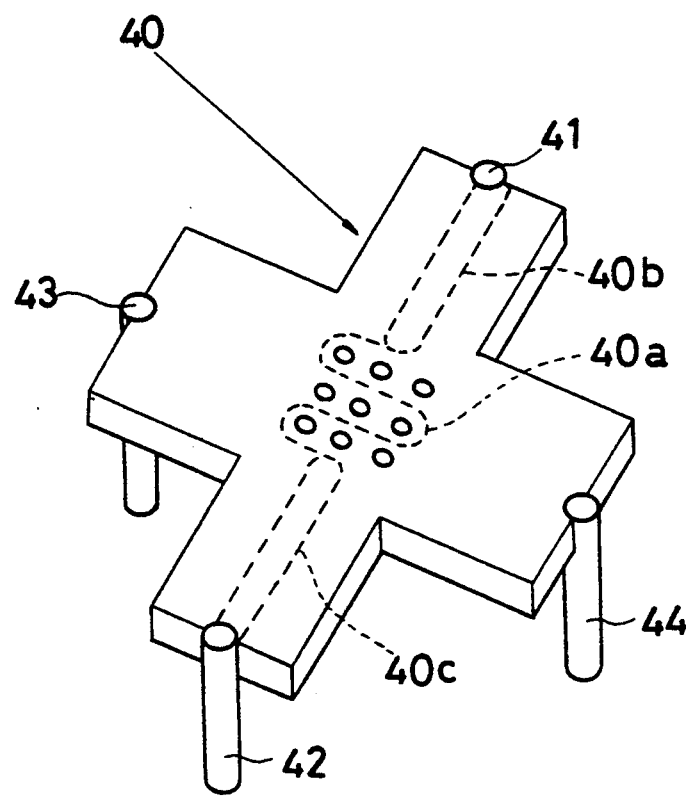
FIGS. 10 through 12 are perspective views of modification forms of this invention.
Figure 11:
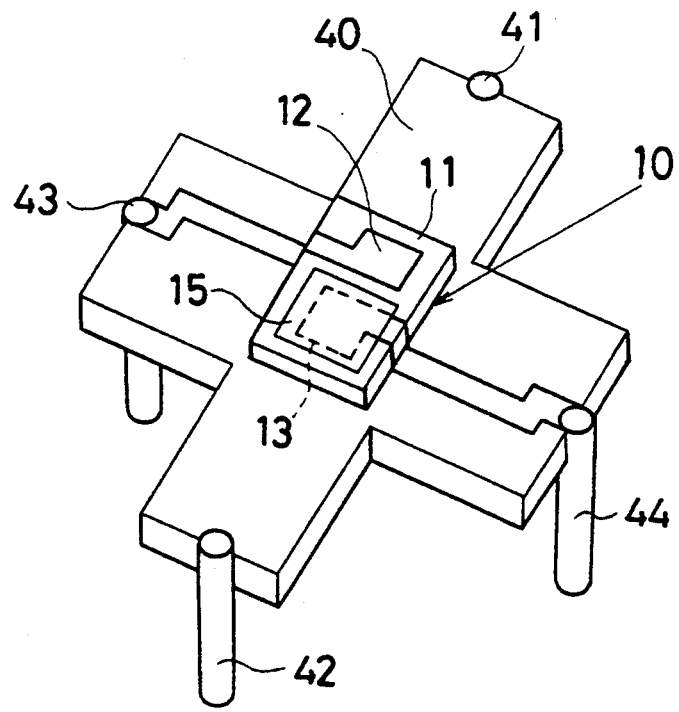
Figure 12:
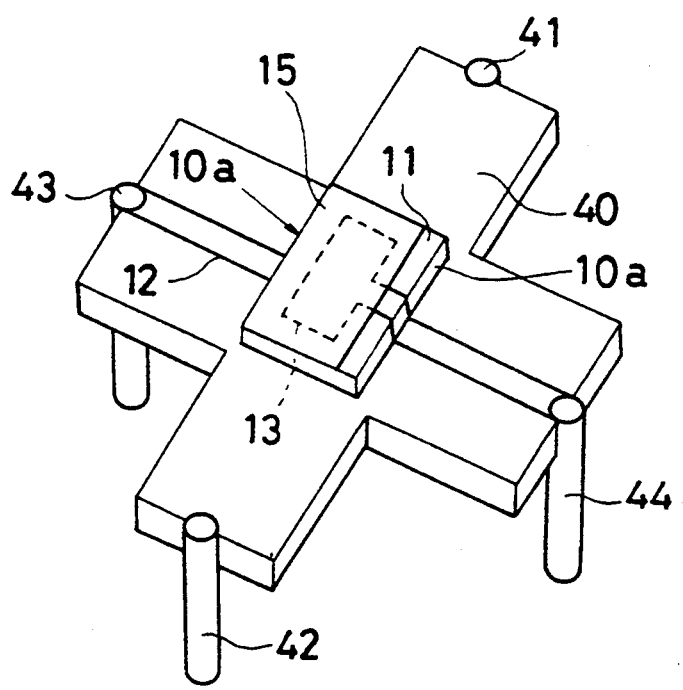

Other modified forms of this invention are described in reference to FIGS. 10 through 12. A ceramic heater 40 has a perforated base made in the form of cruciform configuration. Two terminal of the ceramic heater 40 have conductive patterns 40b, 40c connected at a heater pattern 40a in the center, having nickel pins 41, 42 secured by silver blazing to the ends of the terminals. The other two terminals have nickel pins 43, 44 at the ends for electrical connections to the anode and cathode electrodes 12, 13 of the sensor element.

In FIG. 11, both the anode and cathode electrodes 12, 13 are placed at one side of the oxygen-ion conductive plate 11 to form the sensor element 10.

In FIG. 12, the anode and cathode electrodes 12, 13 are placed in a manner to interpose the oxygen-ion conductive plate 11 to form an electro-chemical cell 10a.

In the above modified forms of this invention, the sensor element 10 is directly placed on the ceramic heater 40, thus contributing to ready manufacturing processes, improved mechanical strength, and good local heating with favorable thermal conductivity for the humidity measurement device.

Although various minor structural modifications might be suggested by those versed in the art, it should be understood that we wish to embody within the scope of the invention hereon all such modifications as reasonably and properly come within the scope of our contribution to the art.

What is claimed is:

1. In a method of measuring humidity by using an electrochemical cell which includes an oxygen-ion conductive solid electrolyte, a porous negative electrode and a porous positive electrode tightly placed on a surface of the electrolyte, the negative electrode being arranged to be partly exposed to a humidity laden gas so that an oxygen component in the gas is transferred from the negative electrode to the positive electrode by a pumping action according to a voltage applied across the pair of electrodes;

the method comprising:

applying a voltage across the pair of electrodes to obtain a characteristic curve between an intensity of the voltage applied and that of an electrical current, the characteristic curve continuously originating from a first flat portion in which a first diffusion limit current remains generally constant with a predetermined voltage range and always passes through a point of inflection with the increase of the applied voltage in which a second differential derivative of the characteristic curve falls on zero at a certain voltage, and ends up with a second flat portion in which a second diffusion limit current remains generally constant with a predetermined voltage range, the point of the inflection being uniquely determined regardless of a humidity level in the gas at constant temperature and oxygen concentration;

reading the point of the inflection, and at the same time, finding the intensity of the first diffusion limit current and the second diffusion limit current; and determining the humidity level in the gas from the fact that the humidity corresponds to a differential value either between the first diffusion limit current and the point of inflection or between the second diffusion limit current and the point of inflection.

2. A method in accordance with claim 1 wherein said electrodes are located on the same surface of the solid electrolyte.

3. A method in accordance with claim 1 wherein said solid electrolyte is located on a ceramic substrate heater to facilitate the conductivity of the oxygen ions.

4. A method in accordance with claim 3 wherein said substrate heater comprises fired alumina and tungsten.

5. A method in accordance with claim 1 wherein the solid electrolyte comprises a solid solution or zirconium oxide and yttrium.

6. A method in accordance with claim 1 wherein said negative electrode is at least partially coated with a porous alumina layer and a glazed layer.

7. A method in accordance with claim 1 wherein said negative electrode provides a porous connection portion which serves as an aperture for limiting the oxygen diffusion and aqueous diffusion.

8. A method in accordance with claim 1 wherein said electrodes are covered by a solid electrolyte provided with a hole communicating a positive electrode portion and the gas to be measured.

* * * * *